United States Patent
Ashley

(10) Patent No.: US 6,176,857 B1
(45) Date of Patent: Jan. 23, 2001

(54) METHOD AND APPARATUS FOR APPLYING THERMAL ENERGY TO TISSUE ASYMMETRICALLY

(75) Inventor: John E. Ashley, San Francisco, CA (US)

(73) Assignee: Oratec Interventions, Inc., Menlo Park, CA (US)

(*) Notice: Under 35 U.S.C. 154(b), the term of this patent shall be extended for 0 days.

(21) Appl. No.: 09/158,320

(22) Filed: Sep. 22, 1998

Related U.S. Application Data

(60) Provisional application No. 60/064,833, filed on Oct. 22, 1997.

(51) Int. Cl.[7] ..................................................... A61B 18/04
(52) U.S. Cl. .............................. 606/32; 606/41; 607/102
(58) Field of Search .................................. 606/32, 41, 50; 607/98, 99, 101, 102, 113

(56) References Cited

U.S. PATENT DOCUMENTS

| | | |
|---|---|---|
| 2,090,923 | 8/1937 | Wappler . |
| 3,178,728 | 4/1965 | Christensen . |
| 3,579,643 | 5/1971 | Morgan . |
| 3,776,230 | 12/1973 | Neefe . |
| 3,856,015 | 12/1974 | Iglesias . |
| 3,867,728 | 2/1975 | Substad et al. . |
| 3,879,767 | 4/1975 | Substad . |
| 3,886,600 | 6/1975 | Kahn et al. . |
| 3,938,198 | 2/1976 | Kahn et al. . |
| 3,945,375 | 3/1976 | Banko . |
| 3,987,499 | 10/1976 | Scharbach et al. . |
| 3,992,725 | 11/1976 | Homsy . |
| 4,043,342 | 8/1977 | Morrison, Jr. . |

(List continued on next page.)

FOREIGN PATENT DOCUMENTS

| | | |
|---|---|---|
| 3511107 A1 | 2/1986 | (DE) . |
| 3632197 A1 | 3/1988 | (DE) . |
| 39 18316 | 3/1990 | (DE) . |

(List continued on next page.)

OTHER PUBLICATIONS

Buchelt et al., Lasers In Surgery and Medicine:Erb:YAG and Hol:YAG Laser Ablation of Meniscus and Intervertebral Discs, vol. 12 No. 4, (1992) pp. 375–381.

Leu et al., Der Orthopade: Endoskopie der Wirbelsaule: Minimal–invasive Therapie, vol. 21, (1992) pp. 267–272.

Phillips et al., JMRI: MR Imaging of Ho: YAG Laser Diskectomy with Histologic Correlation, vol. 3 No. 3, May/Jun. 1993.

(List continued on next page.)

*Primary Examiner*—Linda C. M. Dvorak
*Assistant Examiner*—Roy Gibson
(74) *Attorney, Agent, or Firm*—Wilson, Sonsini, Goodrich & Rosati

(57) ABSTRACT

Systems and methods are described for treating tissue with thermal energy while minimizing the amount of thermal energy to which adjacent tissue is exposed. A surgical instrument for delivering thermal energy to a section of tissue during percutaneous surgery, includes: an elongated shaft having a proximal end and a distal end; and a split tip electrode coupled to the distal end, the split tip electrode i) including a first component and a second component coupled to the first component, and ii) defining a principle axis. The thermal energy is delivered to the section of tissue so as to heat the section of tissue asymmetrically with regard to the principle axis of the split tip electrode. The systems and methods provide advantages in that thermal energy can be directed to one side of the split tip so that a first of two juxtaposed areas of a surgical site can be heated while a second of the two juxtaposed layers is substantially not heated. In alternate embodiments a portion of the site may be actively cooled while an adjacent portion of the site may be actively cooled.

9 Claims, 10 Drawing Sheets

U.S. PATENT DOCUMENTS

| | | |
|---|---|---|
| 4,074,718 | 2/1978 | Morrison, Jr. . |
| 4,085,466 | 4/1978 | Goodfellow et al. . |
| 4,129,470 * | 12/1978 | Homsy . |
| 4,134,406 | 1/1979 | Iglesias . |
| 4,224,696 * | 9/1980 | Murray et al. . |
| 4,224,697 * | 9/1980 | Murray et al. . |
| 4,326,529 * | 4/1982 | Doss et al. . |
| 4,344,193 * | 8/1982 | Kenny . |
| 4,362,160 * | 12/1982 | Hiltebrandt . |
| 4,375,220 * | 3/1983 | Matvias . |
| 4,381,007 * | 4/1983 | Doss . |
| 4,397,314 * | 8/1983 | Vaguine . |
| 4,476,862 | 10/1984 | Pao . |
| 4,483,338 * | 11/1984 | Bloom et al. . |
| 4,517,965 * | 5/1985 | Ellison . |
| 4,517,975 * | 5/1985 | Garito . |
| 4,590,934 | 5/1986 | Malis et al. . |
| 4,593,691 * | 6/1986 | Lindstrom et al. . |
| 4,597,379 * | 7/1986 | Kihn et al. . |
| 4,601,705 | 7/1986 | McCoy . |
| 4,651,734 | 3/1987 | Doss et al. . |
| 4,811,733 | 3/1989 | Borsanyi et al. . |
| 4,815,462 | 3/1989 | Clark . |
| 4,823,791 * | 4/1989 | D'Amelio et al. ............... 123/303.14 |
| 4,838,859 | 6/1989 | Strassmann . |
| 4,846,175 | 7/1989 | Frimberger . |
| 4,873,976 | 10/1989 | Schreiber . |
| 4,894,063 | 1/1990 | Nashef . |
| 4,895,148 | 1/1990 | Bays et al. . |
| 4,907,585 | 3/1990 | Schachar . |
| 4,907,589 | 3/1990 | Cosman . |
| 4,924,865 | 5/1990 | Bays et al. . |
| 4,944,727 | 7/1990 | McCoy . |
| 4,950,234 | 8/1990 | Fujioka et al. . |
| 4,955,882 | 9/1990 | Hakky . |
| 4,966,597 | 10/1990 | Cosman . |
| 4,976,709 | 12/1990 | Sand . |
| 4,976,715 | 12/1990 | Bays et al. . |
| 4,998,933 | 3/1991 | Eggers et al. . |
| 5,007,908 | 4/1991 | Rydell . |
| 5,009,656 | 4/1991 | Reimels . |
| 5,085,657 | 2/1992 | Ben-Simhon . |
| 5,085,659 | 2/1992 | Rydell . |
| 5,098,430 | 3/1992 | Fleenor . |
| 5,100,402 | 3/1992 | Fan . |
| 5,103,804 | 4/1992 | Abele et al. . |
| 5,114,402 | 5/1992 | McCoy . |
| 5,152,748 | 10/1992 | Chastagner . |
| 5,178,620 | 1/1993 | Eggers et al. . |
| 5,186,181 | 2/1993 | Franconi et al. . |
| 5,191,883 | 3/1993 | Lennox et al. . |
| 5,192,267 | 3/1993 | Shapira et al. . |
| 5,201,729 | 4/1993 | Hertzmann et al. . |
| 5,201,730 | 4/1993 | Easley et al. . |
| 5,201,731 | 4/1993 | Hakky . |
| 5,213,097 | 5/1993 | Zeindler . |
| 5,230,334 | 7/1993 | Klopotek . |
| 5,242,439 | 9/1993 | Larsen et al. . |
| 5,242,441 | 9/1993 | Avitall . |
| 5,261,906 | 11/1993 | Pennino et al. . |
| 5,267,994 | 12/1993 | Gentelia et al. . |
| 5,275,151 | 1/1994 | Shockey et al. . |
| 5,279,559 | 1/1994 | Barr . |
| 5,284,479 | 2/1994 | de Jong . |
| 5,304,169 | 4/1994 | Sand . |
| 5,308,311 | 5/1994 | Eggers et al. . |
| 5,311,858 | 5/1994 | Adair . |
| 5,320,115 | 6/1994 | Kenna . |
| 5,323,778 | 6/1994 | Kandarpa et al. . |
| 5,334,193 | 8/1994 | Nardella . |
| 5,342,357 | 8/1994 | Nardella . |
| 5,348,554 | 9/1994 | Imran et al. . |
| 5,352,868 | 10/1994 | Denen et al. . |
| 5,354,331 | 10/1994 | Schachar . |
| 5,364,395 | 11/1994 | West, Jr. . |
| 5,366,443 | 11/1994 | Eggers et al. . |
| 5,366,490 | 11/1994 | Edwards et al. . |
| 5,382,247 | 1/1995 | Cimino et al. . |
| 5,397,304 | 3/1995 | Truckai . |
| 5,401,272 | 3/1995 | Perkins . |
| 5,415,633 | 5/1995 | Lazarus et al. . |
| 5,423,806 | 6/1995 | Dale et al. . |
| 5,433,739 | 7/1995 | Sluijter et al. . |
| 5,437,661 | 8/1995 | Rieser . |
| 5,437,662 | 8/1995 | Nardella . |
| 5,441,503 * | 8/1995 | Considine et al. ................... 606/115 |
| 5,451,223 | 9/1995 | Ben-Simhon . |
| 5,458,596 | 10/1995 | Lax et al. . |
| 5,464,023 | 11/1995 | Viera . |
| 5,465,737 | 11/1995 | Schachar . |
| 5,484,403 | 1/1996 | Yoakum et al. . |
| 5,484,432 | 1/1996 | Sand . |
| 5,484,435 | 1/1996 | Fleenor et al. . |
| 5,487,757 | 1/1996 | Truckai et al. . |
| 5,498,258 | 3/1996 | Hakky et al. . |
| 5,500,012 | 3/1996 | Brucker et al. . |
| 5,507,812 | 4/1996 | Moore . |
| 5,514,130 | 5/1996 | Baker . |
| 5,524,338 | 6/1996 | Martyniuk et al. . |
| 5,527,331 | 6/1996 | Kresch et al. . |
| 5,536,247 * | 7/1996 | Thornton ............................... 604/49 |
| 5,542,920 | 8/1996 | Cherif Cheikh . |
| 5,569,242 | 10/1996 | Lax et al. . |
| 5,599,356 | 2/1997 | Edwards et al. . |
| 5,630,839 | 5/1997 | Corbett, III et al. . |
| 5,681,282 | 10/1997 | Eggers et al. . |
| 5,683,366 | 11/1997 | Eggers et al. . |
| 5,688,270 | 11/1997 | Yates et al. . |
| 5,697,909 | 12/1997 | Eggers et al. . |
| 5,718,702 | 2/1998 | Edwards . |
| 5,728,795 | 3/1998 | Bays . |
| 5,800,482 * | 9/1998 | Pomeranz et al. ................... 607/101 |
| 5,810,809 | 8/1998 | Rydell . |
| 5,836,875 * | 11/1998 | Webster, Jr. ......................... 600/374 |
| 5,853,409 * | 12/1998 | Swanson et al. ...................... 606/31 |
| 5,916,158 * | 6/1999 | Webster, Jr. ......................... 600/374 |
| 5,919,188 * | 7/1999 | Shearon et al. ........................ 606/41 |
| 5,954,665 * | 9/1999 | Ben-Haim ............................ 600/515 |
| 6,014,590 * | 1/2000 | Whayne et al. ...................... 607/122 |

FOREIGN PATENT DOCUMENTS

| | | |
|---|---|---|
| 0 257 116 A1 | 2/1988 | (EP) . |
| 0 274 705 A1 | 7/1988 | (EP) . |
| 0 479 482 A1 | 8/1992 | (EP) . |
| 0 572 131 A1 * | 1/1993 | (EP) . |
| 0 558 297 A2 | 1/1993 | (EP) . |
| 0 542 412 A1 | 5/1993 | (EP) . |
| 0 521 595 A2 | 7/1993 | (EP) . |
| 0 566 450 A1 | 10/1993 | (EP) . |
| 0 682 910 A1 | 11/1995 | (EP) . |
| 0 479 482 B1 | 1/1996 | (EP) . |
| 0 729 730 A1 | 4/1996 | (EP) . |
| 0 737 487 A2 | 10/1996 | (EP) . |
| 0 783 903 A1 | 7/1997 | (EP) . |
| 1122634 | 11/1956 | (FR) . |
| 2 645 008 | 10/1990 | (FR) . |
| 1 340 451 | 12/1973 | (GB) . |
| 2 164 473 | 3/1986 | (GB) . |
| 5-42166 | 5/1993 | (JP) . |
| 637118 | 12/1978 | (SU) . |
| WO 82/02488 | 8/1982 | (WO) . |

| | | |
|---|---|---|
| WO 85/02762 * | 4/1985 | (WO) . |
| WO 92/05828 | 4/1992 | (WO) . |
| WO 92/10142 | 6/1992 | (WO) . |
| WO 93/01774 * | 4/1993 | (WO) . |
| WO 93/16648 | 9/1993 | (WO) . |
| WO 93/20984 | 10/1993 | (WO) . |
| WO 95/01814 | 1/1995 | (WO) . |
| WO 95/20360 * | 3/1995 | (WO) . |
| WO 95/10981 | 4/1995 | (WO) . |
| WO 95/13113 | 5/1995 | (WO) . |
| WO 95/18575 | 7/1995 | (WO) . |
| WO 95/25471 | 9/1995 | (WO) . |
| WO 95/30377 | 11/1995 | (WO) . |
| WO 95/30373 * | 11/1995 | (WO) . |
| WO 95/34259 | 12/1995 | (WO) . |
| WO 96/11638 | 4/1996 | (WO) . |
| WO 96/32051 | 10/1996 | (WO) . |
| WO 96/32885 | 10/1996 | (WO) . |
| WO 96/34559 | 11/1996 | (WO) . |
| WO 96/34568 | 11/1996 | (WO) . |
| WO 96/34571 | 11/1996 | (WO) . |
| WO 96/39914 | 12/1996 | (WO) . |
| WO 97/06855 | 2/1997 | (WO) . |
| WO 98/07468 | 2/1998 | (WO) . |
| WO 98/17190 | 4/1998 | (WO) . |

OTHER PUBLICATIONS

Bromm et al., Human Neurobiology: Nerve Fibre Discharges, Cerebral Potentials and Sensations Induced by CO2 laser Stimulation, vol. 3, (1984) pp. 33–40.

Kolarik et al., Photonucleolysis of Intervertebral Disc and it's Herniation, vol. 51, (1990) pp. 69–71.

Vorwerck et al., Laserablation des Nucleus Pulposus: Optische Eigenschaften von Degeneriertem Bandscheibengewebe im Wellenlangenbereich von 200 bis 2200nm, vol. 151 No. 6, (1989) pp. 725–728.

Wolgin et al., Excimer Ablation of Human Intervertebral Disc at 308 Nanometers, vol. 9, (1989) pp. 124–131.

Davis, Early experience with Laser Disc Decompression, vol. 79 No. 1, (1992) j. Florida M.A.

Quigley et al., Laser Discectomy: Comparison of System, vol. 19 No. 3 (1994) pp. 319–322.

Mehta et al., The Treatment of Chronic back Pain: A Preliminary survey of the Effect of Radiofrequency Denervation of the Posterior Vertebral Joints, vol. 34 (1979) pp. 768–775.

Patil et al., Percutaneous Discectomy Using the Electomagnetc Field Focusing Probe: A Feasability Study.

McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).

Sminia et al., Effects of 434 MHz Microwave Hyperthermia applied to the rat in the region of the cervical Spinal Cord, vol. 3 No. 5 (1987) pp. 441–452.

Sluijter et al., Treatment of Chronic Back and Neck Pain by Percutaneous Therman Lesions, vol. 3 (1981).

Sluijter M.E., The Use of Radiofrequency lesions For Pain Relief in Failed Back Patients, vol. 10 No. 1 (1988).

Cosman et al., Theoretical Aspects of Radiofrequency lesions in the Dorsal Root Entry Zone, vol. 15 No. 6 (1984) pp. 945–950.

Wilkins et al., Neurosurgery: Method of Making Nervous System Lesions, ch. 337, pp. 2490–2499.

Yonezawa et al., The System and Procedure of percutaneous Intradiscal Laser Nucleotomy, vol. 15 No. 5 (1990) pp. 1175–1185.

Kolarik et al., Photonucleolysis of Interverebral Disc and It's Herniation, (1990).

Gottlob et al., Lasers In Surgery And Medicine: Holmium:YAG Laser Ablation of Human Intervertebral Disc: Preliminary Evaluation, vol. 12, (1991) pp. 86–91.

Buchelt et al., Lasers In Surgery And Medicine: Fluorescence Guided Excimer Laser Ablation of Intervertebral Discs In Vitro, vol. 11, (1991) pp. 280–286.

Choy et al., Percutaneous Laser Disc Decompression: A New Therapeutic Modality, vol. 17 No. 8, (1992) pp. 949–956.

Sluijter et al., Persistant Pain, Modern Methods of Treatment: Treatment of Chronic Back and neck Pain, vol. 3, (1981) pp. 141–179.

Sluijter, Int Disabil Studies: The use of Radio Frequency Lesions For Pain Relief in Failed Back, vol. 10, Sep. 4, 1996, pp. 37–43.

Shatz et al., CJS JCC Preliminary Experience With Percutaneous Laser Disc Decompression in the Treatment of Sciatica, vol. 38 No. 5, Oct. 1995 pp. 432–436.

Gerber et al., Der Orthopade: Offene Laserchirurgie am Bewegungsapparat, vol. 25, (1996) pp. 56–63.

Sluyter, Radiofrequency Lesions in the Treatment of Cervical Pain Syndromes, Radionics, Inc. (1989).

Kelly L.E., Purification and Properties of a 23kDa Ca2+–binding Protein, (1990) 271, pp. 661–666.

Gehring W. J., Exploring the Homeobox, (1993), pp. 215–221.

Christian, C. et al., "Allograft Anterior Cruciate Ligament Reconstruction with Patellar Tendon: An Endoscopic Technique", *Operative Technique in Sports Medicine*, vol. 1, No. 1, Jan. 1993, pp. 50–57.

Houpt, J. et al., "Experimental Study of Temperature Distributions and Thermal Transport During Radiofrequency Current Therapy of the Intervertebral Disc", *Spine*, vol. 21, No. 15, (1996), pp. 1808–13.

Troussier, B. et al., "Percutaneous Intradiscal Radio–Frequency Thermocoagulation: A Cadaveric Study", *Spine*, vol. 20, No. 15, (Aug. 1995), pp. 1713–18.

Beadling, L., "Bi–Polar electrosurgical devices: Sculpting the future of arthroscopy ", *Orthopedics today*, vol. 17, No. 1, Jan. 1997, 4 pages.

Ellman International Mfg., Inc., 1989, Catalog, pp. 1–15, 20.

Cosset, J. M., Resistive Radiofrequency (Low Frequency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

Auhll, Richard A., "The Use of the Resectoscope in Gynecology." Biomedical Business International, Oct. 11, 1990, pp. 91–93.

Trimedyne, The Less Invasive Laser Advantage, Omni Spinal Introduction System.

PRNewswire (Dec. 12, 1994), Two Physicians Perform First Outpatient Cervical Disc Procedure Using Laser Technology.

Introduction to the LDD Disc Kit, Oct. 16, 1996.

Mayer et al., Lasers in Percutaneous Disc Surgery: Beneficial Technology or Gimmick?, vol. 25 No. 251 (1993) pp. 38–44.

Schatz et al., Preliminary Experience With Percutaneous Laser Disc Decompression in the Treatment of Sciatica, vol. 38 No. 5, Oct. 1995, pp. 432–436.

Savitz M. A., Same–day Microsurgical Arthroscopic lateral–approach Laser–assisted (SMALL) Fluoroscopic Discectomy, vol. 80, Jun. 1994 pp. 1039–1045.

Bosacco et al., Functional Results of Percutaneous Laser Discectomy, Dec. 1996, pp. 825–828.

* cited by examiner

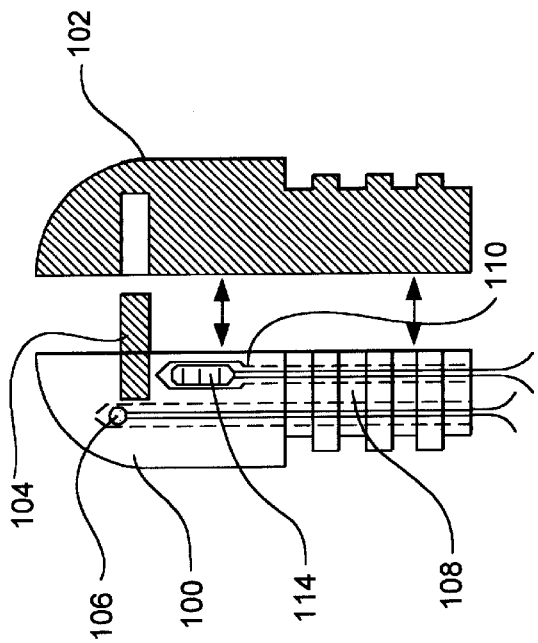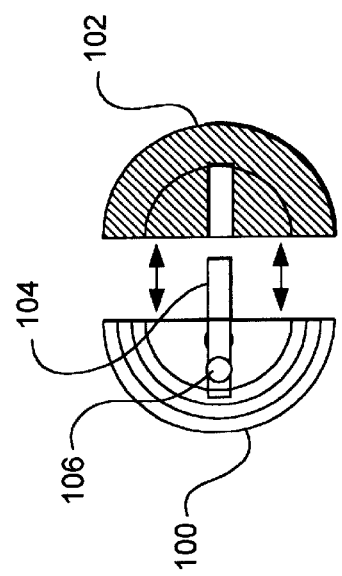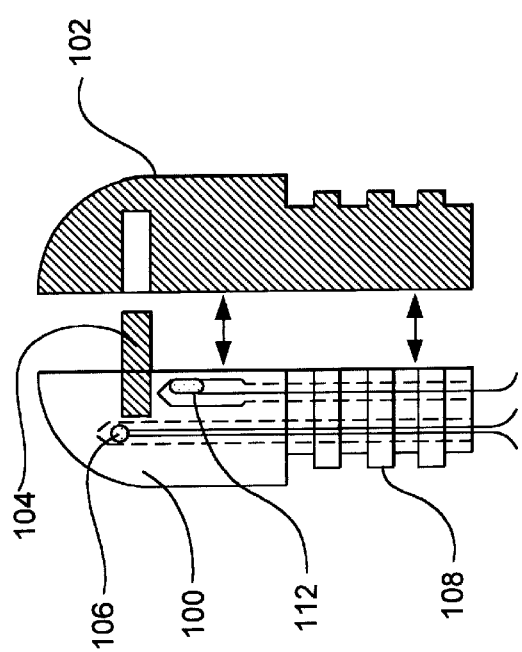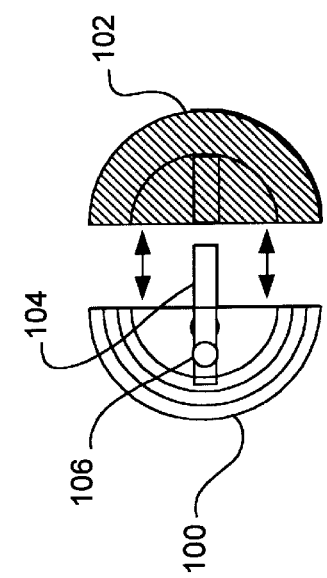
FIG. 1A
FIG. 1B (RF TYPE)
FIG. 1C
FIG. 1D (COIL TYPE)

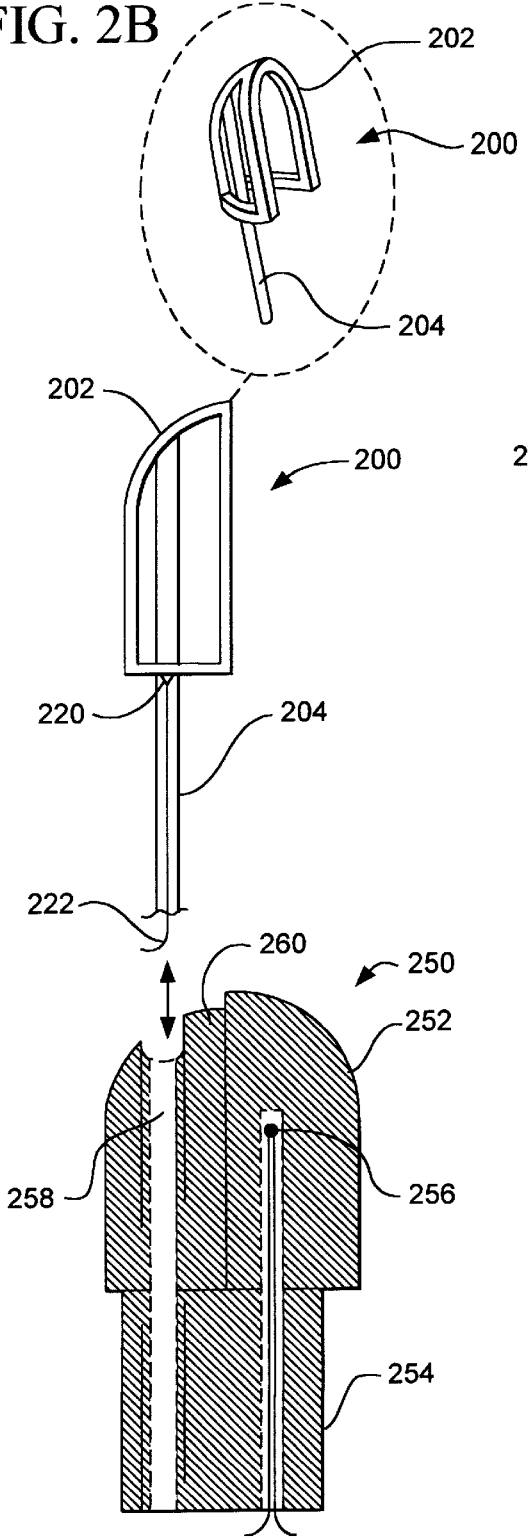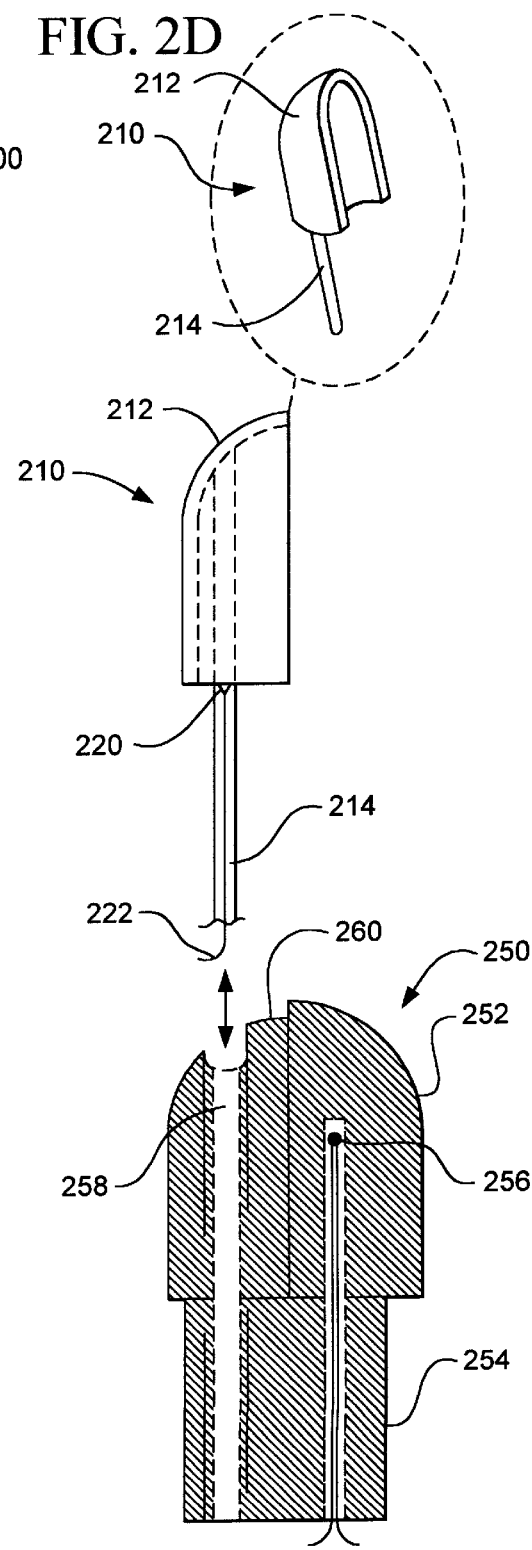

(RF TYPE)

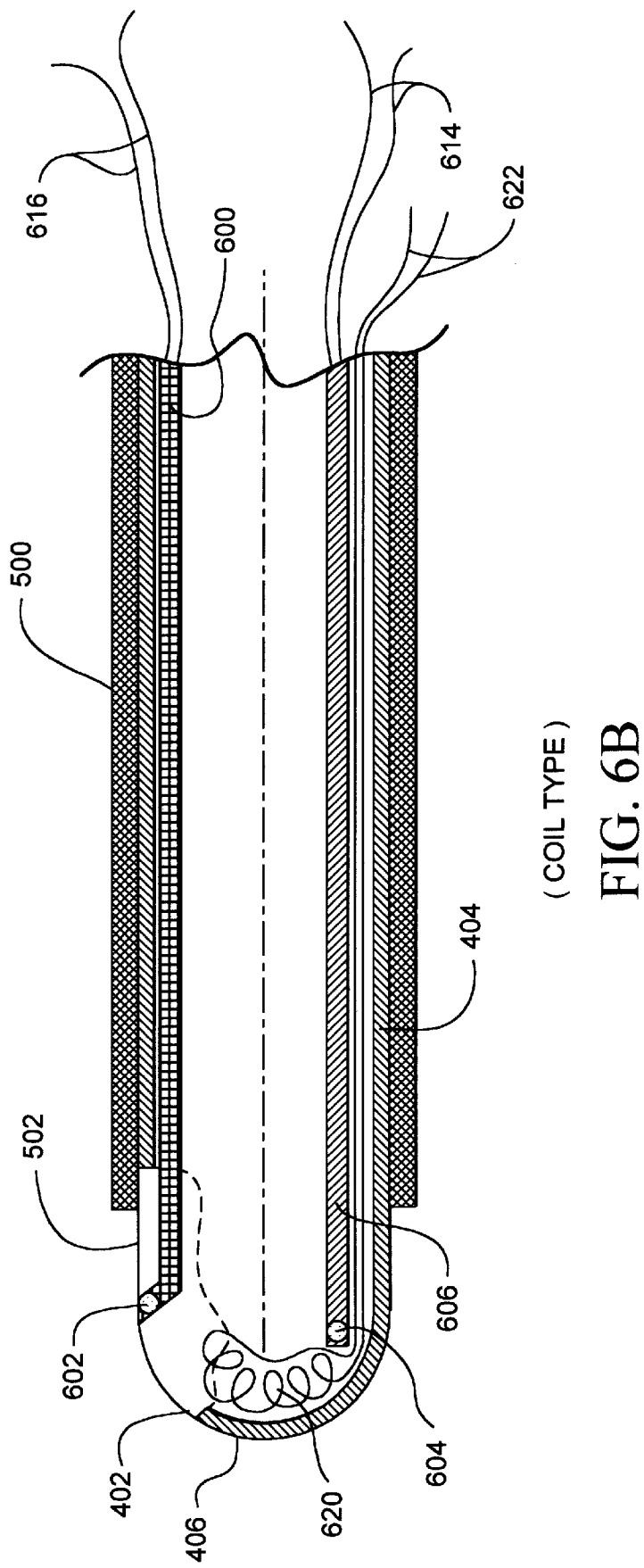
FIG. 6B (COIL TYPE)

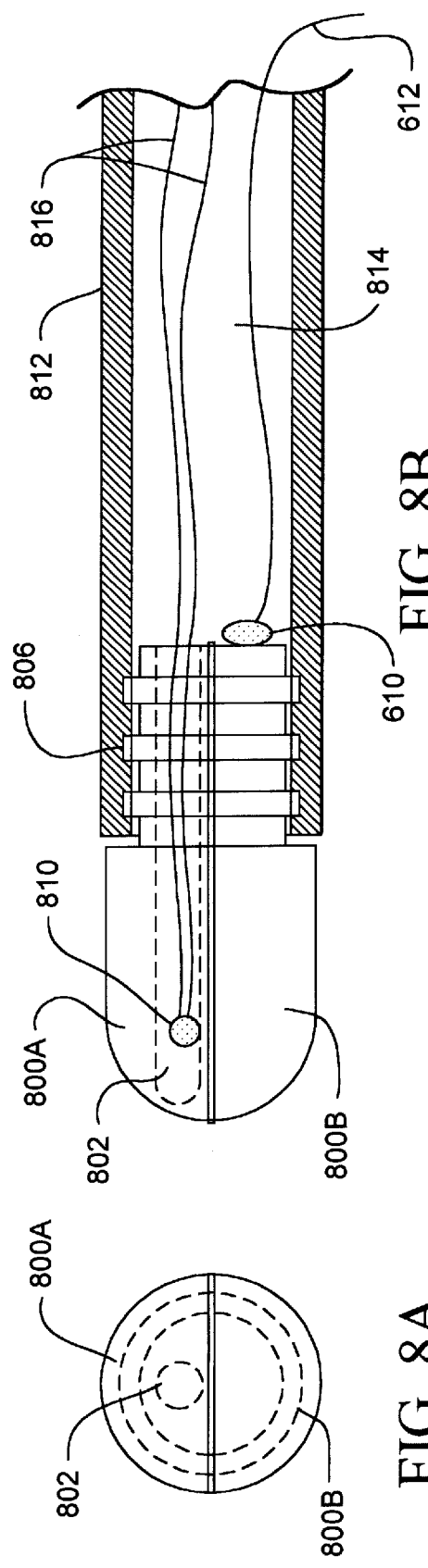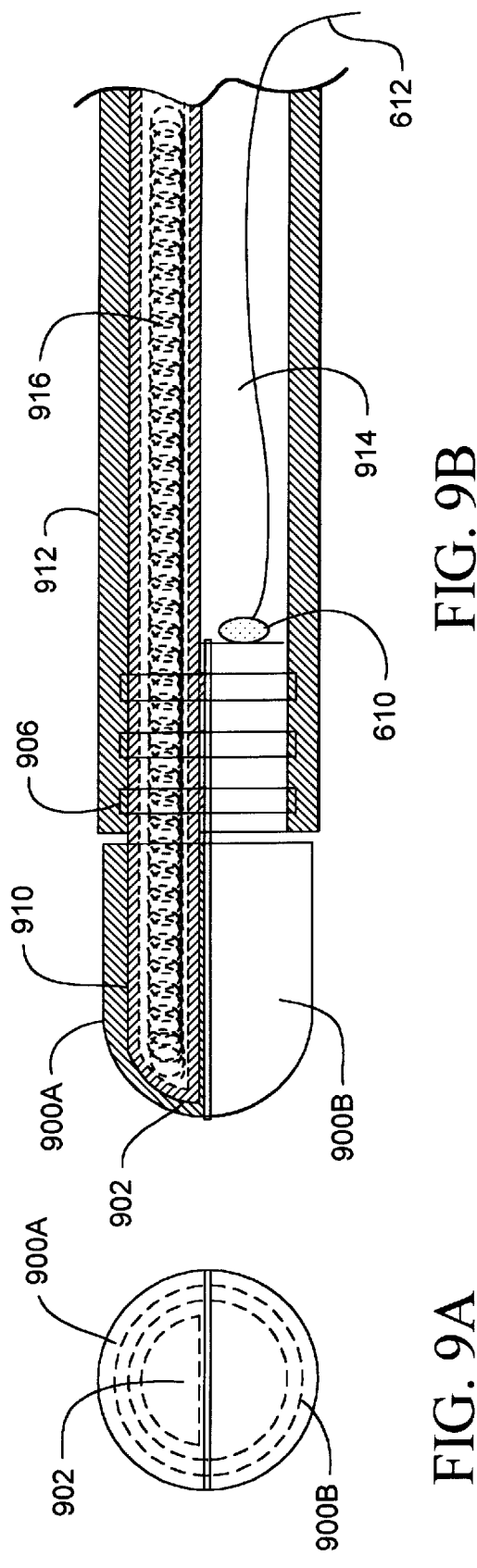

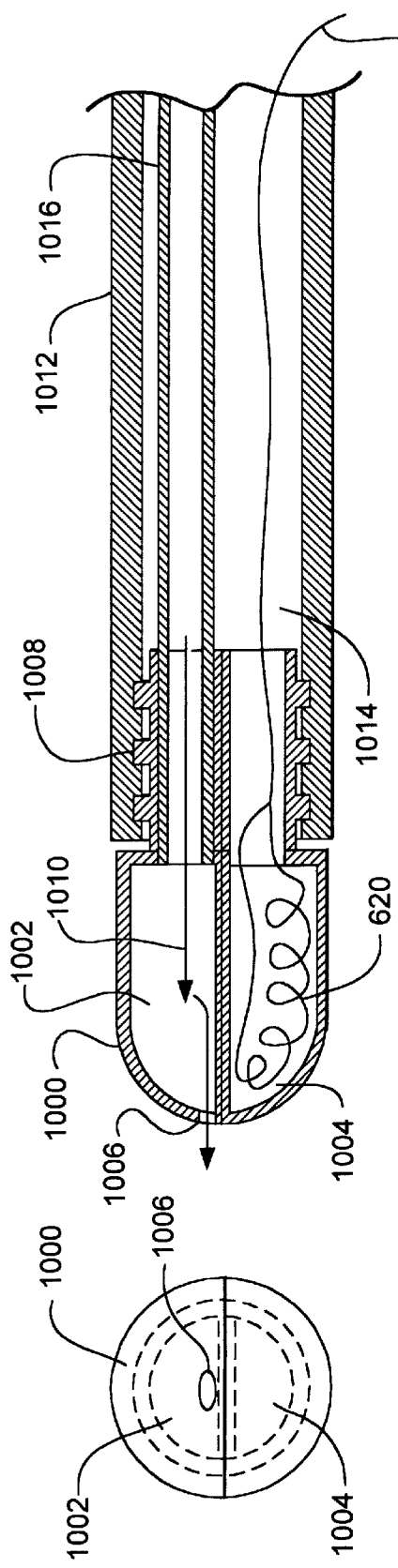
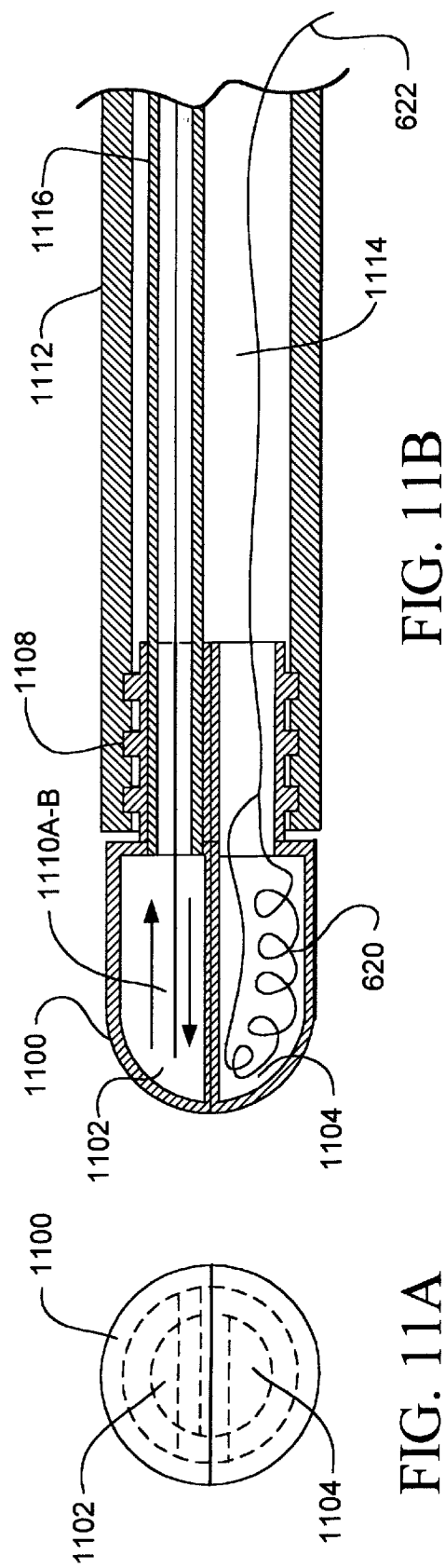
FIG. 10A
FIG. 10B
FIG. 11A
FIG. 11B

METHOD AND APPARATUS FOR APPLYING THERMAL ENERGY TO TISSUE ASYMMETRICALLY

CROSS-REFERENCES TO RELATED APPLICATION

This application is a continuation-in-part under 35 U.S.C. § 120 of copending U.S. Ser. No. 60/064,833, filed Oct. 22, 1997, now pending, the entire contents of which are hereby incorporated herein by reference as if fully set forth herein.

BACKGROUND OF THE INVENTION

1. Field of the Invention

The present invention relates generally to the field of surgery. More particularly, the present invention relates to methods and apparatus for applying thermal energy to tissue during percutaneous surgery. Specifically, a preferred implementation of the present invention relates to an elongated catheter with a longitudinally split tip for directing thermal energy toward one side of the catheter during percutaneous surgery. The present invention thus relates to a surgical method and apparatus of the type that can be termed split tip.

2. Discussion of the Related Art

There has been previous medical experience with the use of surgical apparatus for delivery of thermal energy to tissue during percutaneous intervention. Prior art apparatus for applying thermal energy to tissue, sometimes called electrode tips, have been powered by radio frequency (RF) generators. For example, see U.S. Pat. Nos. 5,458,596; 5,514,130; and 5,569,242, the entire contents of which are hereby incorporated herein by reference as if fully set forth herein. U.S. Pat. Nos. 5,458,596; 5,514,130 and 5,569,242 disclose a controlled amount of thermal energy being delivered from a distal end of an electrode and an RF power source connected to a proximal end of the electrode.

However, a limitation of this technology has been that tissue that is to be treated by exposure to thermal energy is often close to tissue that should not be exposed to the thermal energy, resulting in potentially adverse affect to otherwise healthy tissue. Therefore, what is needed is a solution that permits thermal energy to be directed to the tissue to be treated without exposing nearby tissue to the thermal energy.

For example, intervertebral discs contain collagen that can be effectively treated with thermal energy to repair and/or reinforce the disc. However, there are spinal nerves on the outside of intervertebral discs next to the posterior and the posterior lateral areas of the discs. While the discs can be thermally treated, the spinal nerves should not be thermally treated.

Another example would be in brain surgery where a pathologic lesion could be treated by heating. However, the lesion would be surrounded by other very sensitive tissues that should not be treated.

Heretofore, the prior art has only provided general electrode tips. The electrode tips of the prior art do not have the capability of delivering heat to only one side of the tip. The electrode tips of the prior art have not been designed in a way that would allow the surgeon to place the electrode tip in between two layers of tissue and only provide the therapy to one of those two layers (i.e., to one side of the electrode tip). As a result of these limitations, the prior art tips run a risk of causing injury and necrosis to sensitive tissue. Heating and death of sensitive tissue (e.g., a spinal nerve root) can lead to loss of sensation and mechanical control of various parts of the body (e.g., the foot) or, as another example, loss of bowel control. In the brain the effects being risked could be very devastating.

SUMMARY OF THE INVENTION

A primary object of the invention is to provide an apparatus for, and a method of, heating a section of tissue asymmetrically with regard to a principle axis of an electrode tip. Another object of the invention is to provide an apparatus for, and a method of, heating a first of two juxtaposed layers of tissue without substantially heating a second of the juxtaposed layers of tissue.

In accordance with these objects, there is a particular need for a surgical instrument with a split tip electrode for directing thermal energy toward one side of the surgical instrument during percutaneous surgery. Thus, it is rendered possible to simultaneously satisfy the above-discussed requirements of i) heating a section of tissue asymmetrically with regard to a principle axis of the electrode and ii) heating a first of two juxtaposed layers without substantially heating the second of the two juxtaposed layers, which, in the case of the prior art cannot be satisfied.

A first embodiment of the invention is based on a surgical instrument for delivering thermal energy to a section of tissue during percutaneous surgery, comprising: an elongated shaft having a proximal end and a distal end; and a split tip electrode coupled to said distal end, said split tip electrode i) including a first component and a second component coupled to said first component, and ii) defining a principle axis, wherein thermal energy is delivered to said section of tissue so as to heat said section of tissue asymmetrically with regard to said principle axis of said split tip electrode.

A second embodiment of the invention is based on a method for delivering thermal energy to a section of tissue during percutaneous surgery, comprising: providing a surgical instrument having a split tip electrode i) including a first component and a second component coupled to said first component, and ii) defining a principle axis; inserting the split tip electrode into a body to be treated which contains the section of tissue; and delivering thermal energy to said section of tissue so as to obtain a clinical result, or medically therapeutic result, wherein thermal energy is delivered to said section of tissue so as to heat said section of tissue asymmetrically with regard to said principle axis of said split tip electrode.

A third embodiment of the invention discloses a surgical instrument with a probe menber and a tip. The surgical instrument is connectable by way of an energy coupling to an energy source to provide energy to a surgical site. The probe member includes a distal and a proximal end and the proximal end portion includes the energy coupling to the source of energy. The tip is positioned at the distal end of the elongated probe. The tip includes adjacent first and second portions. The first portion is coupled to the energy coupling at the proximal end to provide energy to the surgical site. The second portion is designed to limit energy delivery to the surgical site. In alternate embodiments the second portion is actively cooled by various means to further limit energy delivery to the surgical site.

These, and other, objects and aspects of the present invention will be better appreciated and understood when considered in conjunction with the following description and the accompanying drawings. It should be understood, however, that the following description, while indicating preferred embodiments of the present invention and numerous specific details thereof, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the components and operation of model systems provided with the present invention, will become more readily apparent by referring to the exemplary, and therefore nonlimiting, embodiments illustrated in the drawings accompanying and forming a part of this specification, wherein like reference numerals (if they occur in more than one view) designate the same elements. It should be noted that the features illustrated in the drawings are not necessarily drawn to scale.

FIGS. 1A–B illustrate a partially exploded side and top views of a mushroom shaped tip (RF Type) that has been split into two halves.

FIGS. 1C–D illustrates a partially exploded side and top views of a mushroom shaped tip (Coil Type) that has been split into two halves.

FIGS. 2A–B illustrate an exploded side view of a mushroom shaped tip with an insertable electrode and an isometric view of the insertable electrode.

FIGS. 2C–D illustrate an exploded side view of a mushroom shaped tip with an insertable electrode and an isometric view of the insertable electrode.

FIG. 6B illustrates a sectional side elevation view of an alternative assembly (Coil Type) shown in FIGS. 5A–C.

FIGS. 8A–B illustrate an end view and a sectional side elevation view of a split tip with an heater (RF Type) on one half and active cooling on the other half using a Peltier cell.

FIGS. 9A–B illustate an end view and a sectional side elevation view of a split tip with an heater (RF Type) on one half and active cooling on the other half using a heat transfer tube.

FIGS. 10A–B illustate an end view and a sectional side elevation view of a split tip with an heater (RF Type) on one half and active cooling on the other half using unidirectional fluid flow.

FIGS. 11A–B illustate an end view and a sectional side elevation view of a split tip with an heater (RF Type) on one half and active cooling on the other half using bi-directional fluid flow.

DESCRIPTION OF PREFERRED EMBODIMENTS

Figure 3A:
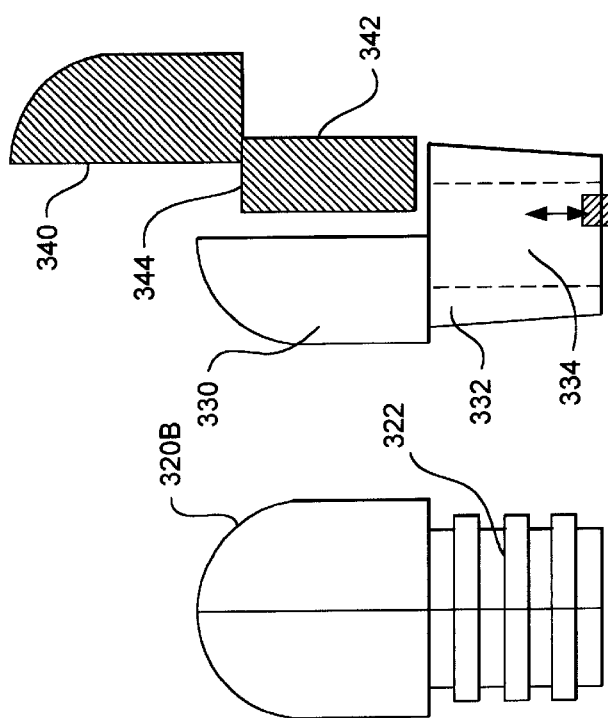
FIG. 3A illustrates a partially exploded view of a shaft and split tip.

The present invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the present invention in detail.

This invention applies to the area of applying thermal energy to tissue during surgery in many different aspects of the body. The invention is especially applicable in those areas of the body where there are specific sensitivities in the surgery being performed such that the prior art does not allow for adequate addressing of the therapeutic need while providing the needed safety element in those certain areas. The reason for that is due to the proximity of tissue which should not be heated next to tissue that is intended to be treated and heated.

FIGS. 1A–D and FIG. 2 show detailed views of alternate embodiments of split tip designs for fastening to the end of a tubular probe of a surgical instrument. Referring to FIGS. 1A/B and 1C/D, the embodiments shown are based on similar tip halves being joined along an atrial centerline. The two embodiments shown are based on a powered electrically conductive half being joined to a passive electrically nonconductive half.

Referring now to FIGS. 1A–B, a conductive half 100 is assembled adjacent a nonconductive half 102. The conductive half 100 is interconnected with the nonconductive half 102 with a pin 104. The conductive half 100 includes a temperature sensor 106. The conductive half also includes an radio frequency power connection 112. Both nonconductive half 102 and conductive half 100 include at a base portion thereof, a plurality of ribs 108. The ribs on both halves can be aligned to define a plurality of continuous ribs to frictionally engage the interior surface of the surgical probe and fasten the tip thereto.

FIGS. 1C–D shows a mushroom shaped structure having a larger diameter portion which is the actual tip of the device. The actual tip of the device is the electrode. The smaller diameter portion is the stem which would be inserted into a shaft of a probe (not shown in FIGS. 1A or 1C). One or both of the stem portions the conductive half 100 and the nonconductive half 102 can be hollow. The split tip in this embodiment is composed of two equal halves of material. A nonshaded half, the conductive half 100 being a conductive material; and, the shaded half, the nonconductive half 102 being an insulating material. By splitting the tip, a device is provided that will conduct electricity and produce a thermal effect on one side of the device but will not conduct electricity on the other side; and, furthermore, will provide a layer of material to prevent thermal conduction from the active side across to the inactive side. The conductive half 100 is again connected to the nonconductive half 102 with a pin 104. The pin is pressed into a hole drilled in each of the halves. The pin 104 provides a mechanism is provided for securing a second piece (i.e., the nonconductive half 102). An adhesive material would provide additional contact (i.e., support for the joint between the two tip halves, conductive half 100 and nonconductive half 102). Alternately, no pin or adhesive may be required when the ribbed portion 108 of the base is of sufficient length to lock the two halves securely one to another within the end of a surgical probe. In this embodiment, an electrical resistance heater 114, for example, a coil, is located at the end of lumen 110. There are two wires connected to the electrical resistance heater 114. The heater could be much longer than illustrated and extend down the split tip electrode into the stem thereof. The temperature sensor 106 in the end of the tip to provide temperature measurements of the heated tip and thereby allow for a precise control of energy delivery to maintain a specific temperature of the tip.

By putting an oscillating AC current into this conductive half 100 through a single electrical wire and having the corresponding electrical wire attached to a pad attached to the skin of a patient, for example, there is generated an electric field which is very concentrated at the tip and very dispersed at the pad, a flow of electrical current takes place, and because of the concentration of the electric field at the tip and the high resistance, the electric field produces heat. The heat itself is caused in the tissue directly because of the current flow and then that heat in the tissue, in turn, heats up this conductive material that is in contact with it. The conductive half 100 could be made out of a number of biocompatible metallic materials that include but are not limited to stainless steel, platinum, gold and silver alloys. Most materials that are highly corrosive produce oxides that are toxic to the body. Gold and silver tend to be less corrosive. Platinum is not corrosive at all, and stainless steel is designed not to corrode.

A typical length of the conductive portion would be about 2 mm and a diameter of about a millimeter and a half. A typical length of the stem would be about 2 mm and a diameter of about a millimeter. That could go up as much as 300% and down by about 50%. Then the other half, the nonconductive half 102, is almost a direct mirror of the first half. There could be a second temperature sensor positioned in a hole drilled into the nonconductive half 102 to be able to monitor the temperature of the cool side for safety purposes. But monitoring the temperature of the cool side is not necessary for functionality. The second side could be an exact duplicate of the first half and the two could be made together.

Alternatively, the device can also be any other split down the middle of a 360° electrode. For instance, one conductive half could be 20% and the nonconductive 80%. A slice could be taken down the middle of any round device. The easiest way to manufacture this may be to make it as a complete round device and then ground it down; fabricate the two round devices and grind them down, so there would be no change in the cost of manufacturing it to change the proportions.

Turning to FIGS. 2A–B and FIGS. 2C–D show two embodiments of a split tip which depart from the two halves designs described above. In the two embodiments shown, RF powered conductive tip electrodes are inserted into almost solid non-conductive base structures that are in-turn inserted into the end of a surgical probe. The solid non-conductive base portion 250 of both embodiments defines an upper portion 252 of a quasi-mushroom shape and a lower base portion 254 of a reduced diameter. The diameter of the lower base portion is dimensional to fit within a probe. A through hole 258 is displaced from the centerline of the tip and extends longitudinally the length of the non-conductive tip. On the same half of the tip where the hole 258 is located, there is also located a recessed portion 260 to accommodate either of the conductive tip electrodes. A temperature sensor 256 is positioned within the non-conductive base.

A first conductive tip wire frame electrode 200 embodiment is shown in FIGS. 2A–B. The electrode is a wire frame structure with a "bow" 202 shaped like the bow of a boat and a shank 204. The shank is connected to the bow. The shank is dimensioned to fit within hole 258 to lock the first conductive tip electrode to the base portion 250 and to position the bow in the recessed portion 260, so that the assembly of bow and base forms a continuous mushroom shaped tip. An RF power termination 220 connects the electrode via wires 222 to an RF supply (not shown). The wires may be positioned within the shank 204. A temperature sensor (not shown) may be connected to the electrode. The wire frame electrode 200 can be coated with a solder or a thin film of metal either before or after it is mated with the nonconducting base portion 250. In this way, the wire frame electrode 200 can act as a skeletal framework for a continuous coating of conductive material. Also, in this way, a thin highly conductive electrode can be provided. For example, a silver solder could be floated over a stainless steel frame. The solder or thin film of metal provides an increased service area which reduces the electrical impedance of the circuit compared to the use of just the wire frame electrode 200.

A second conductive tip electrode embodiment is shown in FIGS. 2C–D. The electrode 210 includes a thin "bow" shaped plate 212 shaped like the bow of a boat and a shank 214. The shank is connected to the bow. The shank is dimensioned to fit within hole 258 to lock the second conductive tip electrode to the base portion 250 and to position the bow in the recessed portion 260, so that the assembly of bow and base forms a continuous mushroom shaped tip. An RF power termination 220 connects the electrode via wires 222 to an RF supply (not shown). The wires may be positioned within the shank 214. A temperature sensor (not shown) may be connected to the electrode.

Thus, in the depicted embodiment, at least three connections would be needed: one for the monopole RF, and two for the temperature sensor (e.g., thermocouple (T, J, E, or K types), thermistor, or resistive wire).

An advantage of the embodiments illustrated in FIGS. 2A–D is that the mass of the conductive portion is reduced. In the embodiments illustrated in FIGS. 1A–D, the conductive and nonconductive portions are separated so as to determine where a current will flow and where it will not. Although the embodiments shown in FIGS. 1A–D address the issue of heat flow from tissue surrounding the conductive portion to tissue surrounding the nonconductive side, the embodiments in FIGS. 2A–2D further improve the heat flow by eliminating more of the mass of the conductive metal. In the embodiments depicted in FIGS. 2A–2D, there is less metal mass to absorb heat from the tissue and, therefore, less metal mass to store heat and transport (i.e., transfer) thermal energy to the cool side. This is the advantage derived from using a smaller amount of metal in the conductive component. The nonconductive portions could also be provided with an active cooling capability, such as, for example, a closed liquid circuit (See FIGS. 8–11).

It can be appreciated that the delivery of thermal energy can be done with a smaller conductive component. However, using a smaller conductive component includes the potential disadvantage of increasing the current density. The limiting factor that determines how small the surface area of the conductive component can be for a particular application is that as the current density goes up, the impedance goes way up and you run the risk of having the tissue char and burn too quickly such that the temperature control mechanism might not function.

The materials that can be used in the embodiments depicted in FIGS. 2A–2D are the same as the materials that can be used in the embodiments depicted in FIGS. 1A–D. The nonconductive thermal/electrical insulating tip materials could be any a number of plastics or ceramics. For example, the thermal/electrical insulating tip materials can be selected from a group that includes fluoropolymers, epoxies, polyamides (nylons), polyetherimide (ULTEM), silicones, polyether ether ketone (PEEK) and polyimides. Any other number of high temperature plastics or ceramics would also be suitable. They should be able to withstand working temperatures of about 150° C., to give a safety factor higher than the temperature which would occur during use of the device in tissue. At the metal portion, the temperature of the tip in the tissue which affects the therapy is anywhere from about 60 to about 85° C.

Turning to FIGS. 3A–D four tip embodiments along with the corresponding surgical probe connection are illustrated. Each of the embodiments shown in FIGS. 3A–D can be implemented either as a split tip, such as those shown in FIGS. 1A–D or the insert type of tip shown in FIGS. 2A–D.

Referring now to FIG. 3A, a snap-fit embodiment for fastening a tip to a probe, is illustrated. A tip including halves 300A–B with a common tapered base 304 and an annular ring 302 intermediate the base and the tip is shown. The probe 350 includes at its distal end a snap fit connector 352. The tip is coupled to the probe 350 by the interlock formed between the snap fit connector 352 and the annular ring 302. By pressing the tip into the probe, the snap fit connector engagages the annular ring thereby forming the interlock to hold the tip within the distal end of the probe.

Figure 3B:
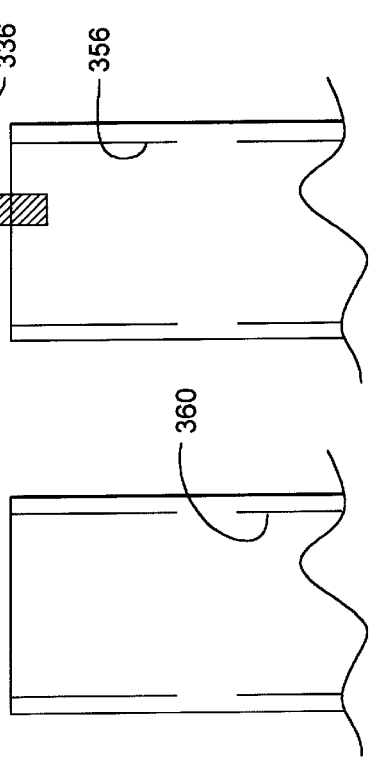
FIG. 3B illustrates a partially exploded view of a shaft and split tip.

FIG. 3B shows a press-fit embodiment for fastening a tip to a probe. A tip including halves 310A–B with a common tapered base 312 and press fit region intermediate the base and the tip is shown. The press fit region is dimensioned for a friction fit with the inside of the distal end of tubular probe 356. The split tip is assembled by press fitting the tip 310A–B into the distal end of the probe to lock the press fit region to the interior surface of the probe.

Figure 3C:
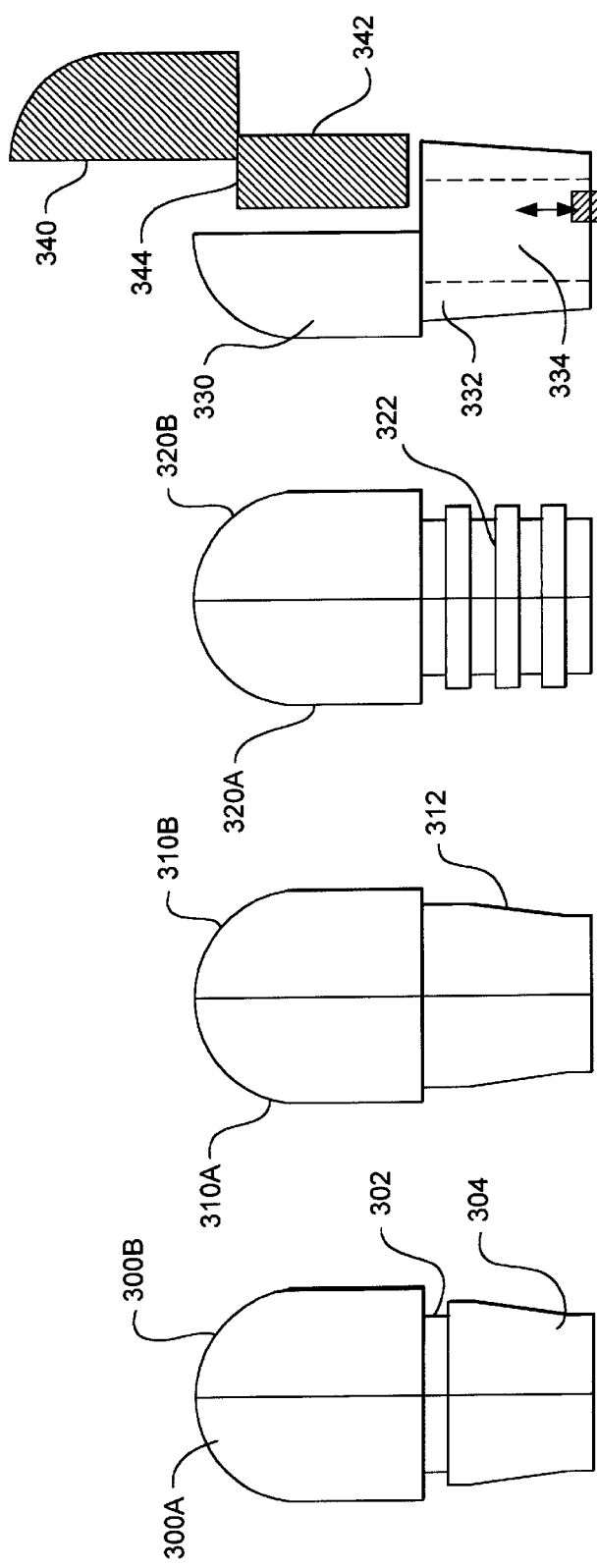
FIG. 3C illustrates a partially exploded view of a shaft and split tip.

Referring now to FIG. 3C, a clearance fit embodiment is illustrated. A tip including halves 320A–B with a common ridged base 322 is shown. The tip is coupled to the interior surface of the annular probe 360 by the frictional engagement of the elastic ridges 322 on the base of the tip with the interior surface at the end of the probe. In an alternate embodiment the ridges are dimensioned for a clearance fit with the interior surface of the probe. Attachment is provided by glue placed on the base of the tip which fills the grooves defined by the ridges and locks the tip to the probe. The ridges provide more surface area and increase the strength of the bond. A cyanoacrylate adhesive is appropriate, as well as some medical grade epoxies and other adhesives.

Figure 3D:
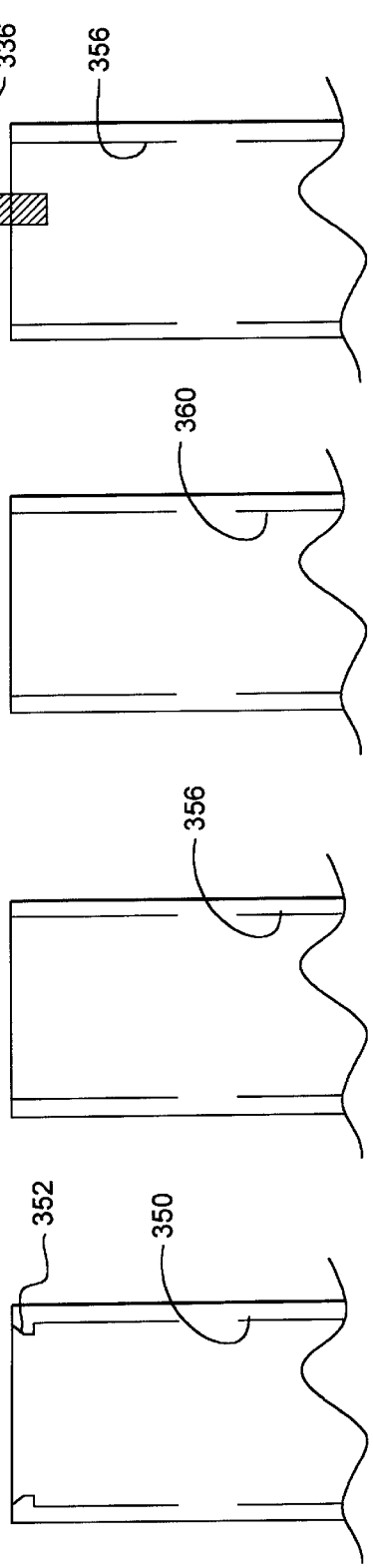
FIG. 3D illustrates a partially exploded view of a shaft and split tip.

FIG. 3D, shows a split tip with asymmetrically conductive half 330 connected to a nonconductive half 340. In this embodiment, the nonconductive half only needs to be restrained from moving out axially rather than radially, as well. The nonconductive half has a stem portion 342 that is much smaller than the stem on the conductive piece and that smaller stem portion can slide into a through hole 334 that extends through at least part (e.g., one half) of the conducting piece's tapered base 332. After the stem portion 342 slides in the hole 334, the stem portion 342 can slide toward the conductive half so that the two opposing halves make contact and form a single mushroom shaped tip. In this position the step 344 that extends past the opposing face of the nonconductive piece is constrained by a corresponding undercut in the conductive half 330 that will prevent it from moving out axially. After the nonconductive half 340 is in place, an interlocking pin 336 can be placed into the through hole 334 of the conductive half so as to wedge the stem of the nonconductive half in that position. Thus, the first component includes a first stem and the second component includes a second stem. The first component is coupled to the second component by inserting the second stem of the second component into a hole formed in the first stem of then first component, then sliding the second component toward the first component, and then inserting a pin between the first stem of the first component and the second stem of the second component. The assembled tip is press fit into the distal end of tubular probe 356 and is held therein by a frictional fit between the tapered base 332 of the conductive half and the interior surface of the distal end of tubular probe 356.

Figure 4A:
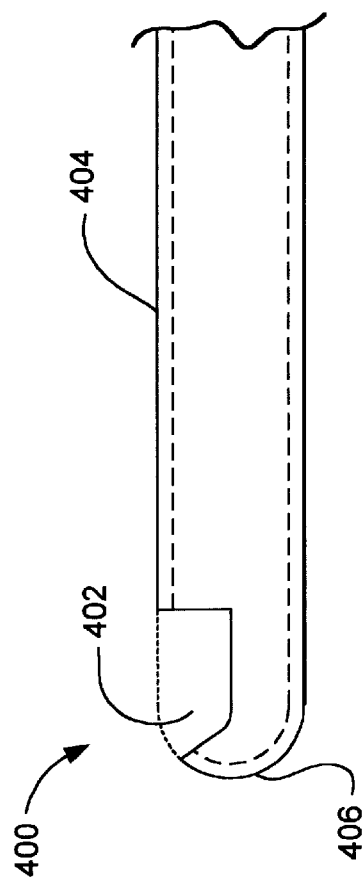
FIGS. 4A–C illustrate side, end, and top views, respectively, of an integrated split tip.
Figure 4B:
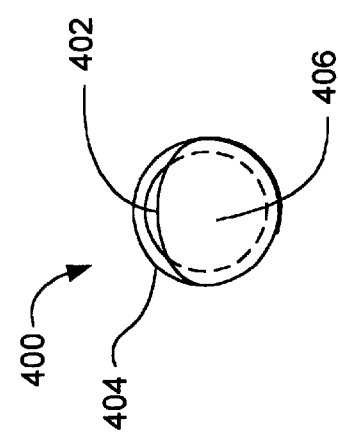
Figure 4C:
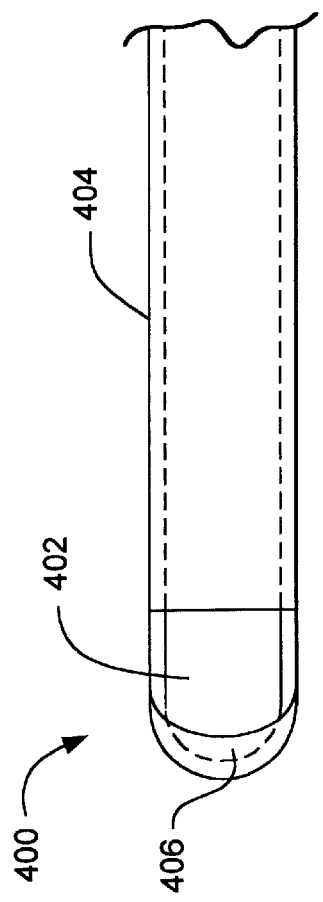

Referring now to FIGS. 4A–C, an integrated tip embodiment 400 is illustrated. FIG. 4A shows a side view. FIG. 4B shows an end-on view. FIG. 4C shows a top view looking down on the shaft. The tip is formed from an tubular probe 404 with a closed distal end 406. The tip is embodied with a split feature, e.g. a naturally cool non-conductive portion formed by cavity 402 at the tip of the probe. The non-conductive portion may be formed by cutting or grinding material from the tubular probe 404 at the end of the probe. The cavity 402 may be filled with a nonconductive material, so it forms a non-conductive portion. The amount of material that's removed and the location of it where it's removed can be used to precisely design the tip. In the embodiment illustrated, approximately one half of the side of the tubular probe 404 has been ground away. However, at the very tip, most of the very tip of the tube (i.e., the spherical, or hemispherical, tip) is preserved. Although part of the very tip is cut away, a lot of it is still preserved and that allows an electrode shape to be created where the tip is conductive and one side is conductive but the other side is not conductive. The wall thickness of the tube could be approximately 0.007" and the internal diameter of the tube could be approximately 0.044". The cavity formed in this area may be filled with an insulating barrier such as silicon to form the non-conductive portion of the tip. Thus when heat either by coil or RF is applied to the tip of the tube, heating only occurs on the side of the tip opposite the insulating cavity 402.

The tip and shaft of the tubular probe 404 may be made from the same tubing by mechanically swagging the ends of the tube together in a constrained radius forming a sealed thin walled tube. This continuous piece of material can be a thin-walled tubing. Such a thin-walled tubing could be mechanically swaged in a correct shape die to form a radius and seal the tip in a bullet or hemisphere-shaped radius. Preferred shaft materials should be strong enough to constrain the tip and provide the support during surgery to locate the split tip electrode where it is needed. The shaft materials could be flexible, or they could be malleable. A thin-walled stainless steel would have the strength required and could be of a size that will allow the surgeon to bend the shaft to access areas within the body that they want to access. The shaft could also be made of an aluminum material so long as the aluminum material was coated on the exterior with a material that was biocompatible. The shaft could also be made of fiber reinforced polyamides, K-resin, ABS, or ULTEM. In the case of an integrated shaft/tip (discussed in more detail below) stainless steel is preferred.

All the split tip electrode designs disclosed herein could also be useful in conjunction with flexible or rigid shafts. They could also be utilized in a directly steerable flexible assembly where a deflecting wire, or a bimetallic strip, or other mechanisms for deflecting flexible would steer the assembly. In the case of a directly steerable flexible assembly, if a flexible plastic was being deflecting, it might be advantageous to add a material between the flexible plastic and any portion of the tip that might get hot. In the designs depicted in FIGS. 2A–D, that might not be necessary because the stem of the device would not get as hot. Even in the case of a nonplastic flexible, or a rigid shaft, if the stem of the split tip electrode is subject to relatively high temperatures, an intermediary material could be usefully located between the split tip electrode and the shaft.

Figure 5A:
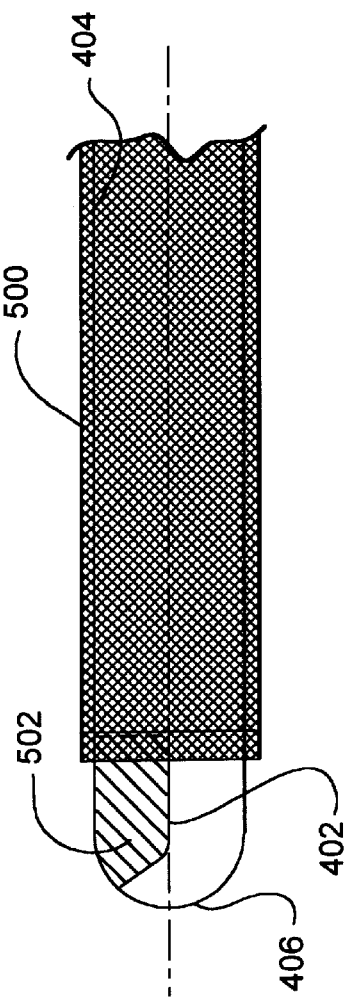
FIGS. 5A–C illustrate side, top, and end views, respectively, of the integrated split tip of FIGS. 4A–C with an insulating shell.
Figure 5B:
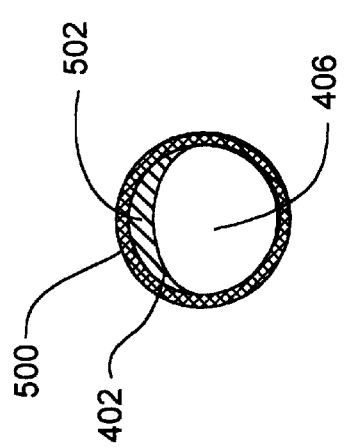
Figure 5C:
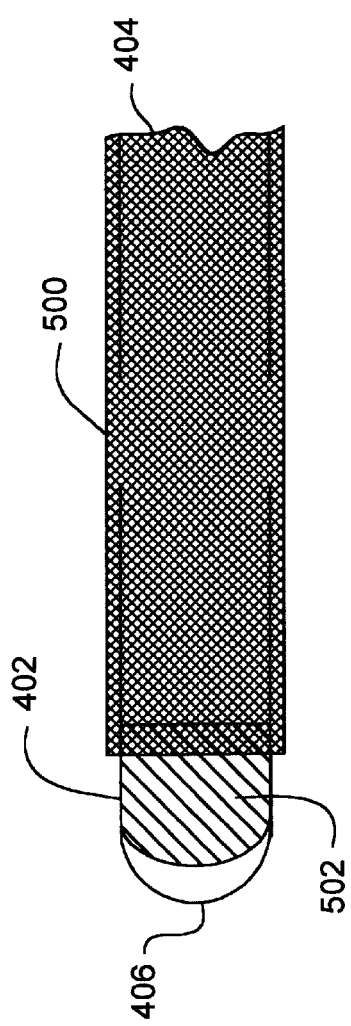

FIGS. 5A–C show the integral probe and split tip discussed above in FIGS. 4A–C. A thermal and electrical tip insulator 502 is positioned in the cavity 402. The insulator 502 serves functionally as both an electrical and thermal insulator to provide a cool nonconductive portion on the tip. This forms an asymmetric geometry at the conducting tip. In addition, an electrical shaft insulating material 500 surrounds the tubular probe 404 along its length, leaving only the tip exposed. These two insulating elements 500–502 are shown in crosshatched portions. The electrical shaft insulating material 500 can include one of the fluoropolymers. This leaves the sensitive portion of the tip exposed so that control of the heat transfer can be performed but the remainder of the surgical instrument is covered with thermally insulating material. The insulation could be approximately 0.003" to 0.006" in thickness. If the probe is stainless steel, the insulator material 500 will be required. Preferable insulators are biocompatible. Preferable insulators include fluoropolymers (e..g., the Teflon family, PTFE, FEP, PFA), silicones, polyamides (nylons), polyimides or ULTEM.

Figure 6A:
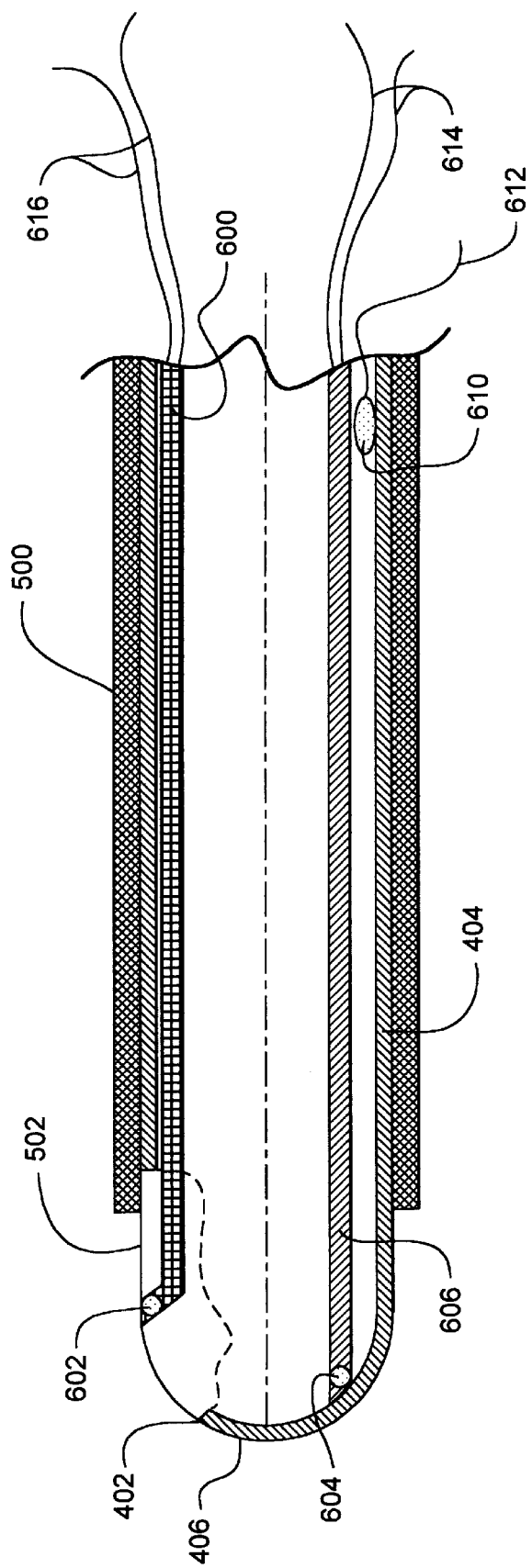
FIG. 6A illustrates a sectional side elevation view of the assembly (RF Type) shown in FIGS. 5A–C.

Referring now to FIGS. 6A–B, elevational cross sections of the integrated probe and electrode shown in FIGS. 4–5 are shown with power and feedback circuitry. In FIG. 6A a first lumen 606 surrounds a first pair of conducting wires 614 that are electrically connected to a first temperature sensor 604. The first temperature sensor 604 is the primary temperature sensor and is located on the inside surface of the conductive tip. A second lumen 600 surrounds a second pair of conducting wires 616 that are electrically connected to a second temperature sensor 602. The second temperature sensor 602 is an optional temperature sensor (e.g., thermocouple) which could be located on the inside surface of the nonconducting material to measure the temperature on the cool insulated portion formed by the cavity 402 of the tip. Preferably the tip wall is thin to reduce the transfer of heat to the insulating material 502, thereby avoiding the heating of sensitive tissue. The open space inside the shaft can be filled with thermal and/or electrical insulating material. A length of 2–4 diameters down from the tip can be advantageously filled with the thermal and/or electrical insulating material so as to help prevent heat from dissipating along the length of the probe. Alternately, the entire inside of the distal end of the shaft and tip can be potted with the thermal and/or electrical insulating material. RF energy is supplied to the tip by a junction 610 connecting wire(s) 612 from an RF power supply to the probe. The connection can advantageously be made to the metal conducting shaft back near the handle (proximal end) of the surgical instrument. In this way, the metal shaft itself becomes the conductor. The shaft electrical insulation material 500 prevents RF energy being conducted anywhere except at the exposed tip.

Referring now to FIG. 6B, a cross section of an alternate embodiment of the integrated probe and split tip using a resistance heater is depicted. In this embodiment, a heater 620 is located near the distal end 406 of the tubular probe 404. The heater 620 is an electrical resistance coil heater powered by a pair of wires 622. The coil wire can be an alloy of approximately 80% nickel and approximately 20% chromium (e.g., nichrom wire). Alternatively, stainless steel could also be used as it provides a reasonable amount of heat. Alloys containing iron would also work as well. For example, 60% iron, but small portions of iron added to a nickel-chromium base would also increase the resistance factor from 1125 up to as much as 1350. This would permit a reduction in the current requirements. The downside of adding iron to the composition is that it is a more expensive material. All remaining portions of the integrated probe and split tip are identical to the embodiment discussed above in FIG. 6A.

Figure 7:
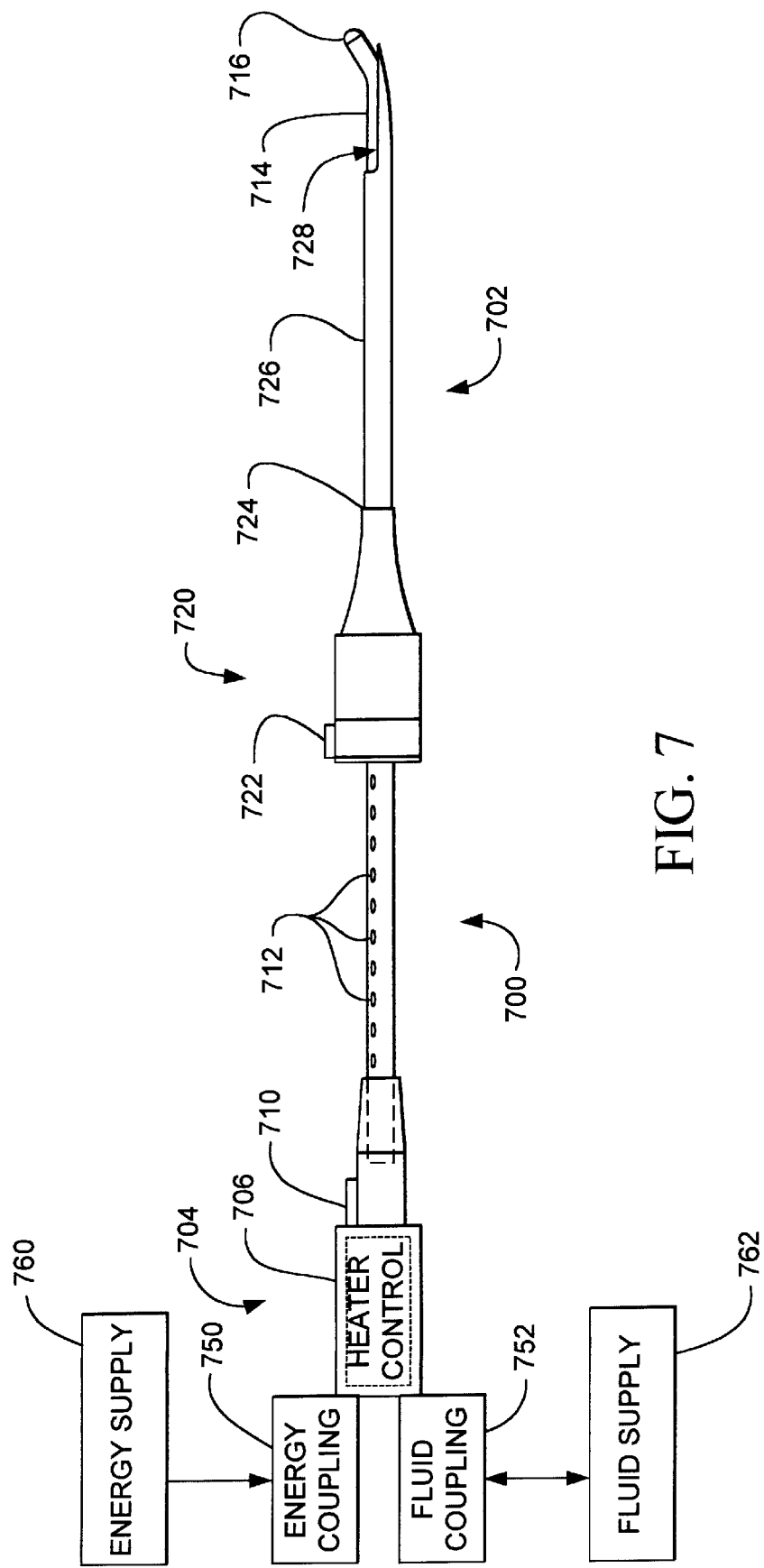
FIG. 7 illustrates an schematic elevational view of a surgical instrument including a split tip electrode.

FIG. 7 shows a surgical instrument utilizing a split tip according to the embodiments described and discussed in this invention. The surgical instrument includes a tubular probe 700 and cannula 702. Tubular probe 700 comprises a handle 704, an orientation indicator 710, a stem 712, a flexible portion 714 and a split tip 716. Handle 704 includes a heater delivery and control circuitry 706. The probe is shown partially within a cannula 702. The cannula includes a hub portion 720, a stem 726 an a tip 728. The hub includes a visual orientation indicator 722 and a stem mount 724.

The handle is coupled to the proximal end of the probe stem 712 while the tip 716 is coupled to the distal end of the probe stem. Energy and Fluid couplings 750–752 link the proximal end of the probe to respectively the energy source 760 and the fluid supply 762. The energy source can in an embodiment of the invention provide RF power. The fluid supply can in an embodiment of the invention pump fluids such as brine to/from the surgical instrument to cool the non-conductive portion of the tip. Indicator 710 on the handle 704 of the tubular probe 700 indicates the direction of curvature of split tip 716 as well as the preferred axis of deflection of the flexible portion 714 of the probe. Visual depth indicators on the stem 712 of the tubular probe 700 indicate the extent to which the probe protrudes from the tip 728 of the cannula 702. Visual indicator 722 on the hub portion 720 of cannula 702 indicates the orientation of the opening in the tip 728 of the cannula 702. It is this opening on the tip 728 of the cannula from which the probe extends within the surgical site.

FIGS. 8–11 show split tip embodiments in which the nonconductive half is actively cooled. This potentially provides the advantage of being able to maintain a greater temperature differential between the conductive and nonconductive halves. This allows surgery to be performed at sites immediately adjacent to areas of the body such as nerve endings which are extremely temperature sensitive and which need to be shielded from the effects of the energies associated with thermal or RF surgery.

FIGS. 8A–B show respectively an end view of a split tip and a cross sectional elevation of a split tip and probe assembly. The split tip includes a nonconductive and conductive half respectively 800A–B. The nonconductive half 800A defines a cavity 802 extending from the base of the split tip to just beneath the exterior surface of the end of the split tip. Within the cavity a Peltier junction 810 is shown. The Peltier Effect was discovered in 1834. When current passes through the junction of two different types of conductors it results in a temperature change. Today, bismuth telluride is primarily used as the semiconductor material, heavily doped to create either an excess (n-type) or a deficiency (p-type) of electrons. When used as a heat pump, the module utilizes the Peltier effect to move heat and is called a thermoelectric cooler (TEC). The Peltier junction can produce temperature reductions of 30–40 degrees centigrade below ambient. Wires 816 running the length of the interior portion 814 of the probe 812 link the Peltier junction 810 to an energy source at the proximal end of the probe. The base of the split tip contains a series of ring shape protrusions 806 which frictionally engage the interior surface of the probe 812 and lock the split tips within that probe. The conductive portion 800B of the split tip has an RF junction 610 electrically joining it via wires 612 extending the length of the probe to an energy source in the handle of the surgical tool.

In operation RF energy of a monopolar or bipolar nature applied to the conductive portion 800B of the tip causes localized heating of the surgical sight adjacent to the conductive portion of the tip. On the opposing side of the tip the nonconductive portion 800A may be made of a material which has either a high or low thermal conductivity. Because of the presence of the active cooling source provided by the Peltier junction 810 energy can be removed from the nonconductive portion 800A of the tip. As will be obvious to those skilled in the art resistance coil may be substituted for the RF energy source on the conductive portion 800B of the tip.

FIGS. 9A–B show respectively an end view of a split tip and a cross sectional view of a split tip assembled with a probe in accordance with an alternate embodiment of the invention. In the embodiment shown active thermal transfer in the form of a heat tube withdraws energy selectively from the nonconductive portion of the tip. FIGS. 9A–B show a split tip comprised of a nonconductive and conductive portion respectively 900A–B. Within the nonconductive portion a cavity 902 is formed. The cavity accommodates a heat transfer tube generally 910 which extend from the cavity in the nonconductive portion of the split tip along the length of the interior portion 914 of the probe 912. The split tip base includes a series of flexible rings 906 which frictionally engaged the interior surface of the probe 912 to lock the split tip to the probe. The conductive portion 900B of the tip is linked via an RF junction 610 and wires 612 to an energy source.

In operation RF energy applied in either a monopolar or bipolar fashion or for that matter a resistive coil causes the conductive portion of the split tip to transfer energy to the surgical sight. Any heat that is transferred to the nonconductive portion 900A of the tip is actively removed from that tip and radiated away from the tip by the thermal pipe 910. The thermal pipe in a manner well known to those in the prior art contains a heat transfer fluid 916 the circulation of which tends to transfer heat from the tip along the length of the tube where it is radiated through the walls of the probe 912.

FIGS. 10A–B show respectively an end view of a split tip and a side elevation assembly view of a split tip and probe according to another embodiment of the invention. In this embodiment the nonconductive portion of the tip is actively cooled by a fluid flow of for example a brine solution from along the length of the probe and through an opening in the nonconductive portion of the tip to the surgical sight. This has the advantage of cooling the nonconductive portion of the tip as well as providing a solution to the surgical site to clarify the site and to expand the tissue around the surgical sight. The split tip 1000 includes an actively cooled cavity 1002 and a thermally heated cavity 1004. The actively cooled cavity 1002 extends from the base of the split tip to an exterior opening at the apex of the end of the tip. This portion of the tip is connected to a lumen 1016 which extends the length of the probe through a fluid coupling to a fluid supply. The heated portion of the probe, i.e. the cavity 1004 is shown with a resistive coil 620 connected via wires 622 thru an energy coupling to an energy source. This will be obvious to those skilled in the art this half the probe could alternately be heated by an RF energy source such as that shown in FIGS. 8–9. The tip itself is locked into the probe 1012 by means of ring shaped protrusions 1008 around the circumference of the base. These frictionally engage an interior surface 1014 of the probe and lock the tip into the probe.

In operation, fluid of a brine solution is delivered from a fluid supply along the lumen 1016 provides for a monodirectional flow 1010 through the cooling cavity 1002 and exits the end of the tip at opening 1006. This fluid serves to expand and cleanse the surgical site and to cool the half of the tip which defines the cavity 1002.

FIGS. 11A–B are respectively an end view of the split tip and a cross sectional elevation of the assembly of a split tip and probe. This embodiment is fluid cooled with a bidirectional fluid flow thus does not require the opening in the tip that was discussed above in connection with FIGS. 10A–B. The tip 1100 includes a fluid cooled and heated cavity respectively 1102–1104. The fluid cooled cavity 1102 includes a baffle 1110A–B which accept an incoming fluid stream and returns a heated fluid stream to a pair of dual lumens 1116 which extends the length of the probe 1112 to a fluid supply via a fluid coupling. The base of the split tip is locked by means of annular rings 1108 frictionally with an interior surface of the probe 1114.

In operation electrical energy supplied to resistive coils 1104 from a power source via wires 620 heats the external wall of the split tip adjacent cavity 1102. The dual lumens 1116 deliver and remove brine solution to the nonconducting cavity 1102. This provides bidirectional fluid flow 1110A–B within the cavity which has the effect of removing heat. The disclosed embodiments show either an RF power lead or an electrical resistive coil as the structures for performing the function of heating, but the structure for heating can be any other structure capable of performing the function of heating, including, by way of example a microwave transducer, an ultrasonic transducer, an optical fiber or even a liquid thermal jet.

Specific embodiments of the present invention will now be further described by the following, nonlimiting examples which will serve to illustrate in some detail various features of significance. The examples are intended merely to facilitate an understanding of ways in which the present invention may be practiced and to further enable those of skill in the art to practice the present invention. Accordingly, the examples should not be construed as limiting the scope of the present invention.

While not being limited to any particular performance indicator or diagnostic identifier, preferred embodiments of the present invention can be identified one at a time by testing for the presence of a well defined thermal flux. The test for the presence of a well defined thermal flux can be carried out without undue experimentation by the use of a simple gelatin experiment. Temperature sensors arranged in a three dimensional array within a block of gelatin (simulating tissue) in which a split tip is positioned can measure the temperature increase provided by the delivery of thermal energy from the split tip. Preferred embodiments will exhibit a three-dimensional section of higher temperature on one side of the split tip. Particularly preferred embodiments will exhibit a section that defines a well defined thermal flux (i.e., the section of higher temperature will exhibit smooth three-dimensional isotherms).

A practical application of the present invention that has value within the technological arts is the thermal treatment of an intervertebral disc where spinal nerves are in close proximity to the disc. Further, the present invention is useful in conjunction with the thermal treatment of articulated joint (such as for the purpose of tightening a shoulder joint), or in conjunction with the thermal treatment of lesions (such as for the purpose of treating cancer tumors), or the like. There are virtually innumerable uses for the present invention, all of which need not be detailed here.

A split electrode tip and/or methods that include the use of the split tip electrode, representing embodiments of the invention, can be cost effective and advantageous for at least the following reasons. The invention permits thermal energy to be directed to a section of tissue in need thereof without adversely effecting surrounding sections of tissue. The invention lowers the risk of surgical intervention. The invention can permit less thermal energy to be coupled during the treatment. The invention lowers the amount of time and/or power required to implement a treatment.

All publications, patent applications, and issued patents mentioned in this application are hereby incorporated herein by reference in their entirety to the same extent as if each individual publication, application, or patent was specifically and individually indicated to be incorporated in its entirety by reference.

All the disclosed embodiments of the invention described herein can be realized and practiced without undue experimentation. Although the best mode of carrying out the invention contemplated by the inventors is disclosed above, practice of the present invention is not limited thereto. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Further, although the split tip electrode described herein is a physically separate module, it will be manifest that the split tip electrode may be integrated into the apparatus with which it is associated. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the present invention may be made without deviating from the spirit and scope of the underlying inventive concept. It is intended that the scope of the invention as defined by the appended claims and their equivalents cover all such additions, modifications, and rearrangements. The appended claims are not to be interpreted as including means-plus-function limitations, unless such a limitation is explicitly recited in a given claim using the phrase "means for". Expedient embodiments of the invention are differentiated by the appended subclaims.

What is claimed is:

1. A surgical instrument for delivering energy to a section of tissue during surgery, comprising:
   an elongated probe having a proximal end and a distal end; and
   an electrode coupled to said distal end, said electrode i) including a first component, and a second component coupled to said first component, and ii) defining a principle axis,
   wherein energy is delivered to said section of tissue so as to heat said section of tissue asymmetrically with regard to said principle axis of said electrode,
   wherein said first component includes a thin plate.

2. A surgical instrument for delivering energy to a section of tissue during surgery, comprising:
   an elongated probe having a proximal end and a distal end; and
   an electrode coupled to said distal end, said electrode i) including a first component and a second component coupled to said first component, and ii) defining a principle axis,
   wherein energy is delivered to said section of tissue so as to heat said section of tissue asymmetrically with regard to said principle axis of said electrode,
   wherein said first component is coupled to said second component with a pin.

3. A surgical instrument for delivering energy to a section of tissue during surgery, comprising:
   an elongated probe having a proximal end and a distal end; and
   an electrode coupled to said distal end, said electrode i) including a first component and a second component coupled to said first component, and ii) defining a principle axis,
   wherein energy is delivered to said section of tissue so as to heat said section of tissue asymmetrically with regard to said principle axis of said electrode,
   wherein ii) said first component includes a first stem and said second component includes a second stem and i) first component is coupled to said second component by inserting said second stem of said second component into a hole formed in said first stem of said first component, then sliding said second component toward said first component, and then inserting a pin between said first stem of said first component and said second stem of the second component.

4. A surgical instrument for delivering energy to a section of tissue during surgery, comprising:
   an elongated probe having a proximal end and a distal end; and
   an electrode coupled to said distal end, said electrode i) including a first component and a second component coupled to said first component, and ii) defining a principle axis,
   wherein energy is delivered to said section of tissue so as to heat said section of tissue asymmetrically with regard to said principle axis of said electrode,
   wherein said electrode is coupled to said distal end with a snap-fit connection.

5. A surgical instrument for delivering energy to a section of tissue during surgery, comprising:
   an elongated probe having a proximal end and a distal end; and
   an electrode coupled to said distal end, said electrode i) including a first component and a second component coupled to said first component, and ii) defining a principle axis,
   wherein energy is delivered to said section of tissue so as to heat said section of tissue asymmetrically with regard to said principle axis of said electrode,
   wherein said electrode is coupled to said distal end with a friction-fit connection.

6. A surgical instrument for delivering energy to a section of tissue during surgery, comprising:
   an elongated probe having a proximal end and a distal end; and an electrode coupled to said distal end, said electrode i) including a first component and a second component coupled to said first component, and ii) defining a principle axis, wherein energy is delivered to said section of tissue so as to heat said section of tissue asymmetrically with regard to said principle axis of said electrode, wherein said elongated probe includes a round tube that is integrally joined to said first component and said second component is located in an opening that is formed in said round tube.

7. A method for delivering energy to a section of tissue during surgery, comprising:

providing a surgical instrument having an electrode i) including a first component and a second component coupled to said first component, and ii) defining a principle axis;

inserting the electrode into a body to be treated which contains said section of tissue; and delivering energy to said section of tissue so as to obtain a medically therapeutic result, wherein energy is delivered to said section of tissue so as to heat said section of tissue asymmetrically with regard to said principle axis of said electrode, wherein inserting includes inserting said surgical instrument into an intervertebral disc.

8. A surgical instrument connectable by way of an energy coupling to an energy source to provide energy to a surgical site, said surgical instrument comprising:

a probe member including a distal and a proximal end and the proximal end portion including the energy coupling to the source of energy; and a tip positioned at the distal end of said elongated probe, said tip including adjacent first and second portions and the first portion coupled to the energy coupling at the proximal end to provide energy to the surgical site and the second portion designed to limit energy delivery to the surgical site, and further comprising:

a heat transfer tube extending from the second portion of the tip along a length of the probe, and the heat transfer tube coupled thermally to the second portion of the tip to remove energy from the second portion of the tip.

9. A surgical instrument, connectable by way of an energy coupling to an energy source to provide energy to a surgical site, said surgical instrument comprising:

a probe member including a distal and a proximal end and the proximal end portion including the energy coupling to the source of energy; and a tip positioned at the distal end of said elongated probe, said tip including adjacent first and second portions and the first portion coupled to the energy coupling at the proximal end to provide energy to the surgical site and the second portion designed to limit energy delivery to the surgical site, wherein said surgical instrument is connectable by way of a fluid coupling to a fluid supply, and the distal end of the probe member further comprising the fluid coupling to the fluid supply; and the tip further comprising a coupling between the second portion and the fluid coupling to provide a fluid from the fluid supply to the second portion and to remove the fluid, so as to remove energy from the second portion.

* * * * *